United States Patent
Fletcher et al.

(10) Patent No.: US 8,735,850 B2
(45) Date of Patent: May 27, 2014

(54) METHOD AND APPARATUS FOR EBEAM TREATMENT OF WEBS AND PRODUCTS MADE THEREFROM

(75) Inventors: P. Michael Fletcher, Chelmsford, MA (US); Arthur Somerstein, Marblehead, MA (US); James Hoffmaster, Needham, MA (US); Michael Lawrence Bufano, Belmont, MA (US); Stephen Whittacker Into, Harvard, MA (US)

(73) Assignee: Hitachi Zosen Corporation, Osaka (JP)

( * ) Notice: Subject to any disclaimer, the term of this patent is extended or adjusted under 35 U.S.C. 154(b) by 137 days.

(21) Appl. No.: 12/830,910

(22) Filed: Jul. 6, 2010

(65) Prior Publication Data

US 2011/0006225 A1 Jan. 13, 2011

Related U.S. Application Data

(60) Provisional application No. 61/223,446, filed on Jul. 7, 2009, provisional application No. 61/288,569, filed on Dec. 21, 2009.

(51) Int. Cl.
*B65D 55/08* (2006.01)
*B65D 1/02* (2006.01)

(52) U.S. Cl.
USPC ............... 250/455.11; 422/22; 250/492.3

(58) Field of Classification Search
USPC .............. 250/305, 492.1, 492.3, 455.11; 422/26–28, 33, 22
See application file for complete search history.

(56) References Cited

U.S. PATENT DOCUMENTS

| | | | | |
|---|---|---|---|---|
| 4,409,775 A | * | 10/1983 | Brody et al. | 53/167 |
| 5,489,783 A | * | 2/1996 | Kristiansson | 250/492.3 |
| 5,635,714 A | * | 6/1997 | Nablo et al. | 250/305 |
| 5,962,995 A | | 10/1999 | Avnery | |
| 6,674,229 B2 | | 1/2004 | Avnery et al. | |
| 6,919,570 B2 | | 7/2005 | Avnery | |
| 6,949,222 B1 | * | 9/2005 | Moller et al. | 422/62 |
| 7,329,885 B2 | | 2/2008 | Avnery et al. | |
| 7,417,239 B2 | | 8/2008 | Naslund et al. | |
| 2002/0197184 A1 | * | 12/2002 | Palaniappan | 422/22 |
| 2004/0086421 A1 | * | 5/2004 | Moller et al. | 422/22 |

(Continued)

FOREIGN PATENT DOCUMENTS

| | | |
|---|---|---|
| JP | 2004 053509 | 2/2004 |
| WO | WO 02/061464 | 8/2002 |

OTHER PUBLICATIONS

Sloan, Mary, PCT Invitation to Pay Additional Fees and, Where Applicable, Protest Fee, Patent Cooperation Treaty, International Searching Authority, Int'l Filing No. PCT/US2010/001904, Int'l Filing Date: Jul. 6, 2010, Document Dated Sep. 16, 2010, 6 pages, Rijswijk, Netherlands.

(Continued)

*Primary Examiner* — Jack Berman
*Assistant Examiner* — Wyatt Stoffa
(74) *Attorney, Agent, or Firm* — Fildes & Outland, P.C.

(57) ABSTRACT

A method and apparatus for sterilization of webs and products made therefrom using electron beams (ebeams) is provided. A controller is configured to modulate an ebeam to ensure that a non-continuously moving web is sterilized within a desired range of exposure. During sterilization in place operations, manifolds are configured to operate to ensure that sterilants do not enter an irradiation zone to prevent damage to ebeam emitters.

7 Claims, 4 Drawing Sheets

(56) References Cited

U.S. PATENT DOCUMENTS

| | | |
|---|---|---|
| 2006/0145093 A1* | 7/2006 | Naslund et al. .............. 250/492.1 |
| 2006/0163499 A1* | 7/2006 | Echigo et al. ............. 250/492.22 |
| 2006/0284111 A1* | 12/2006 | Naslund et al. .............. 250/492.1 |
| 2007/0187027 A1 | 8/2007 | Tausch et al. |
| 2007/0253859 A1* | 11/2007 | Hill ................................... 422/3 |
| 2007/0283666 A1* | 12/2007 | Py et al. ............................ 53/425 |
| 2009/0013646 A1* | 1/2009 | Mastio et al. .................... 53/425 |
| 2009/0035479 A1* | 2/2009 | Rangwalla .................... 427/504 |
| 2009/0110613 A1* | 4/2009 | Naka et al. ...................... 422/186 |
| 2009/0148340 A1* | 6/2009 | Hansen et al. .................. 422/22 |
| 2010/0132307 A1* | 6/2010 | Nishino et al. .................. 53/167 |
| 2010/0148065 A1* | 6/2010 | Kivlehan ...................... 250/310 |
| 2011/0012030 A1* | 1/2011 | Bufano et al. .............. 250/492.3 |
| 2011/0012032 A1* | 1/2011 | Bufano et al. .............. 250/492.3 |
| 2011/0062347 A1* | 3/2011 | Eguchi et al. ............. 250/455.11 |
| 2011/0085938 A1* | 4/2011 | Carbone et al. ................. 422/29 |
| 2011/0198513 A1* | 8/2011 | Holm ......................... 250/492.3 |
| 2011/0256020 A1* | 10/2011 | Hansen et al. ................... 422/24 |

OTHER PUBLICATIONS

Bufano, et al., Method and Apparatus for Ebeam Treatment of Webs and Products Made Therefrom, U.S. Appl. No. 61/223,446, filed Jul. 7, 2009, 15 pages.

Thomson, et al., Shielding for Electron Beam Sterilization, U.S. Appl. No. 61/288,569, filed Dec. 21, 2009, 44 pages.

* cited by examiner

METHOD AND APPARATUS FOR EBEAM TREATMENT OF WEBS AND PRODUCTS MADE THEREFROM

CROSS REFERENCE TO RELATED APPLICATIONS

The present application claims priority to U.S. Provisional Application No. 61/223,446, filed on Jul. 7, 2009 by Bufano et al., for METHOD AND APPARATUS FOR EBEAM TREATMENT OF WEBS AND PRODUCTS MADE THEREFROM, the contents of which are hereby incorporated by reference.

The present application also claims priority to U.S. Provisional Application No. 61/288,569, filed on Dec. 21, 2009 by Thomson et al., for SHIELDING FOR ELECTRON BEAN STERILIZATION, the contents of which are hereby incorporated by reference.

FIELD OF THE INVENTION

The present invention relates generally to sterilization of packaging materials, and more specifically to sterilization of web based packaging materials using electron beams.

BACKGROUND OF THE INVENTION

Electron beam (ebeam) emitting apparatus have been used over the years to treat moving webs for various purposes, such as to sterilize a web of packaging material, polymerize web material, cure a coating on a web, etc. Of particular interest here is the utilization of such an ebeam to sterilize packaging material. Sterilization of the packaging material typically leads to a longer shelf life of the product that is packaged therein. In the food packaging industry, it is well-known to form various open receptacles from a web made of various materials which are subsequently filled with a product, e.g. a beverage, and then sealed transversely or sealed by adhering another material to the top edge of the receptacle. The receptacles are then separated at spaced-apart locations therealong, creating a succession of individual closed containers. Packaging applications of this kind are typically referred to as either Horizontal Form Fill Seal (HFFS) or Vertical Form Fill Seal (VFFS). In HFFS machines, the forming and filling steps are accomplished as the web is traveling horizontally, or parallel to ground plane. HFFS machines are typically used for cup based products. In VFFS machines, the forming and filling steps are accomplished as the web is traveling vertically, or perpendicular to ground plane. VFSS machines are typically used for packs, stick packs, and bag based products.

As used here, the term "packaging material" generally means packaging is substrates such as polymer films, carton board and multilayer laminates in web and strip form that may be made into product packages such as packs, cartons, pouches, bags, stick-packs, sachets, cups, gable top containers, bag-in-box containers and other containers that may be filled with a food, beverage, pharmaceutical, medical device or other article which should be maintained in an aseptic condition prior to use, as well as such packages already formed from a substrate, both when the packages are empty and already filled with products.

When being sterilized, the packaging material may have to be moved through the irradiation zone of an ebeam emitter in a non-continuous fashion in order to accommodate a processing step being performed on the packaging material by an upstream or downstream machine that requires intermittent slowing or stopping of that material. For example, if the packaging material is a substrate being fed to a forming machine, the substrate movement through that zone may be slowed periodically as that machine transforms the substrate into a succession of containers of one kind or another. Likewise, if the packaging material being sterilized comprises a succession of open containers traveling on a conveyor to a filling machine, the conveyor may have to be stopped briefly or at least slowed while each container is being filled with product.

The dose applied to the packaging material exposed to an ebeam may be calculated as follows:

$$\text{Dose} = \left(\frac{K}{S}\right)i \quad (1)$$

Where:
K=an efficiency constant which depends on multiple parameters of a specific application including: accelerating voltage, distance from electron beam window to is packaging material, other factors affecting the efficiency of electrons reaching the packaging material
S=speed
i=ebeam emitter filament current When the packaging material is required to move non-continuously through the emitter's irradiation zone due to such processing constraints, some portions of that material spend more time in the irradiation zone than others and thus receive a larger ebeam dose than if the electron beam source was kept at constant current and parameters affecting K as described above were kept constant.

In order to maintain a dose delivery to the packaging material that falls within the required range for a particular application it is be desirable to modulate the effective dose delivery as a function of the speed S. However, modifying the ebeam dose applied to the packaging material necessitated by the non-continuous advance thereof may have an adverse effect on the ebeam emitter.

More particularly, a typical electron beam source or emitter includes a vacuum chamber containing an electron generator for generating electrons. The vacuum chamber has an exit window where the electrons, after being accelerated, exit the chamber through that window and are directed to the packaging material being treated. The emitter exit window includes a thin foil which is usually supported by a perforated support plate. During normal operation of the emitter, the exit window will absorb some amount of the electron energy which results in heating of the foil. The amount of energy absorbed by the window is proportional to the current of the beam and inversely proportional to the voltage of the beam. If that heating is excessive, the foil may fail. Since the foil constitutes part of the wall of the vacuum chamber, such a failure will cause the vacuum chamber to lose its vacuum, thereby disabling the emitter.

The thermal stresses on the exit window are particularly great if the emitter output power is cycled rapidly, thereby creating more dramatic thermal cycling of the foil than if the emitter were operated at a constant power output. A known disadvantage of the prior art arrives when the emitter is being used to treat packaging material which is advanced in a non-continuous manner. In such environments, the integrity of the emitter's exit window is directly affected by the ability to manage the heating and cooling cycles of the window.

During web packaging sterilization, the web is drawn from a roll rotatably mounted to a roll stand and conducted to the packaging machine by way of a shielded irradiation compartment or tunnel. The web enters the tunnel through an entry slot and is guided through an irradiation zone in the tunnel where at least one surface of the web is exposed to a beam of electrons of sufficient energy and for a sufficient time to kill or inactivate microorganisms so as to disinfect the surface of the web. The web leaves the irradiation tunnel through an exit slot coupled to the packaging machine in which the web is formed into receptacles, filled, and sealed as described above. An example of such apparatus for sterilizing web used for product packaging is described, for example, in U.S. Pat. No. 7,417,239, entitled METHOD AND DEVICE FOR ELECTRON BEAM IRRADIATION, the contents of which are hereby incorporated by reference.

As seen from the above-incorporated patent, when the sterilizing apparatus is in is operation to remove microorganisms and other particles, it is desirable to maintain a flow of cool air which flows from the packaging machine into the sterilizing apparatus counter to the direction of web travel through the irradiation tunnel. This air flows to exhaust ports located near where the unsterilized web enters the tunnel. The same air flow also sweeps out any ozone that may be present formed by interaction of the electrons with air.

Also, in aseptic applications, such as in the packaging of certain food and pharmaceutical products, before each web run, it is common practice during a sterilization-in-place (SIP) cycle to sterilize the interior surfaces of the sterilizing apparatus and packager by spraying a fluid sterilant such as peracetic acid (PAA) or vaporized hydrogen peroxide (VHP) into the incoming air stream so that the sterilant is circulated throughout the interior of the apparatus including its irradiation tunnel. The sterilant condenses on all interior surfaces of the tunnel thereby sterilizing those surfaces. The sterilant is usually removed by subsequently circulating through the apparatus hot air whose temperature is above that of the sterilant's vaporization temperature and the resulting vapor is drawn out of the apparatus through the exhaust ports.

A known disadvantage of the prior art is that some of that SIP sterilant may damage the electron beam system if substantial amounts of vaporized sterilant come into direct contact with the electron beam window.

SUMMARY OF THE INVENTION

The disadvantages of the prior art are overcome by providing a method and apparatus for sterilization of webs and products made therefrom using electronic beams (ebeams). Illustratively, when packaging material is advanced in a non-continuous manner through the irradiation zone of an electron beam from an ebeam emitter, the ebeam dose delivered to the material is kept within a desired range that will effectively sterilize the material without adversely effecting same. This is accomplished by controlling, as a function of the advance of the material along the process line, the beam energy output from the emitter and/or the "transmission factor" of an electron beam modulator located in the path of the beam so as to maintain the current density of the ebeam at the packaging material in the emitter's irradiation zone with a desired range. The beam energy output from the emitter can be varied while maintaining near-constant thermal load on the window by simultaneously varying current and voltage. The modulator may comprise an electron mask or scatterer or one more movable shutters that that can partially or completely block the beam energy emanating from the emitter's exit window in order to control the electron beam dosage delivered to the substrate. During such treatment of the packaging material, the beam energy output from the emitter may also be controlled as a function of the packaging material advance to maintain the thermal load on the emitter's exit window within a desired range that maximizes the useful life of that window.

Thus, it is contemplated within this invention that the ebeam dose applied by the emitter to the packaging material may be adjusted solely by controlling the beam modulator as a function of the packaging material advance, in which case the electron beam may run at a constant voltage and current. By the same token, the beam modulator may be controlled so as to not interfere with the ebeam at all, leaving the dose being applied to the packaging material controlled solely by regulating the emitter's ebeam current and voltage. In any event, the emitter is controlled to manage the heat load on the emitter's exit window to keep that load within a safe range when delivering the desired ebeam dosage to the packaging material.

In some applications, a web accumulator may be placed between the ebeam irradiation zone and an upstream or downstream processing machine, allowing the packaging material to be advanced through the irradiation zone at a substantially constant speed. In this event, a substantially constant ebeam dose that will not overstress the emitter window may be applied to the material traveling through that zone as set by the controller.

Further, in alternative embodiments, an exhaust manifold serving a multiplicity of web-facing exhaust ports extends the full width of the web upstream from the irradiation zone. The manifolds are connected to an exhaust fan so that the air from tunnel may optionally be drawn through a suitable filter to capture pollutants such as bacteria, particulate matter and ozone gas. It is a feature of the invention that one or more dual-purpose transverse manifolds are supported within housing just downstream from irradiation zone in the direction of web travel.

Typically, filtered air at a desired temperature is introduced into machine via an inlet opening. Preferably, also, before each web run, an SIP cycle is carried out whereby a sterilant is introduced into the incoming air stream by means of a nozzle connected by way of a pump to a sterilant source. When pump is in operation, the sterilant is ejected from nozzles into the air stream and distributed on the interior surfaces of the machine.

Usually, in prior apparatus of this type, some of that sterilant is drawn through conduit into tunnel where it covers surfaces in the irradiation zone of that apparatus thereby producing the adverse consequences described above. To avoid this eventuality, it is a feature of this invention that during the aforesaid SIP cycle, the manifold(s) is/are connected to a vacuum source so that any sterilant entering tunnel via exit slot is swept away before it can reach the irradiation zone.

Preferably, each manifold should be as close as possible to zone so that the SIP sterilant can reach all surfaces downstream from zone but cannot enter that zone. Thus, the tunnel surfaces within zone remain devoid of sterilant and are sterilized only by the electrons in beam B when emitter is operative.

BRIEF DESCRIPTION OF THE DRAWINGS

The above and further advantages of invention may be better understood by referring to the following description in conjunction with the accompanying drawings in which like reference numerals indicate identical or functionally similar elements.

DETAILED DESCRIPTION OF ILLUSTRATIVE EMBODIMENTS

A. Modulation of Window Control

Figure 1:
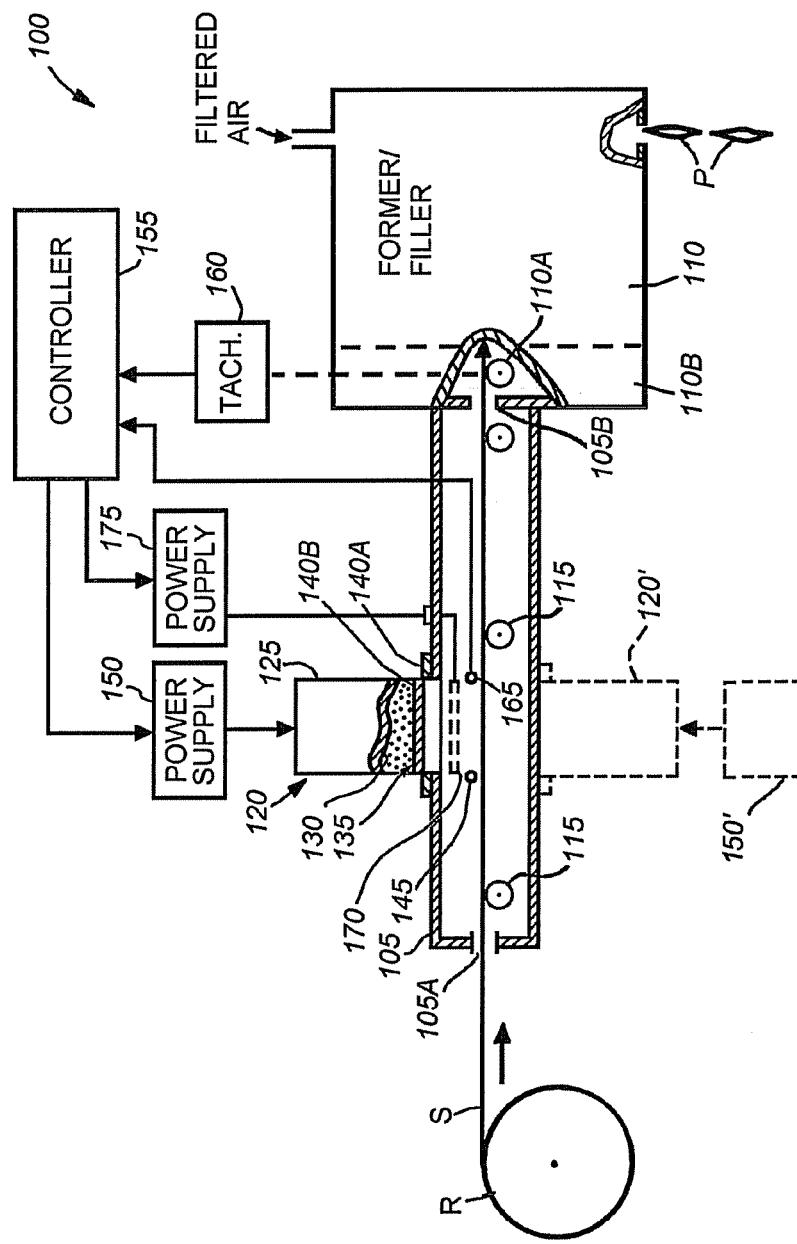
FIG. 1 is a schematic diagram of an exemplary aseptic packaging apparatus environment in accordance with an illustrative embodiment of the present invention.

FIG. 1 illustrates an exemplary aseptic packaging apparatus environment 100 in which a packaging substrate S drawn from a roll R is conducted through a slit 105A at the entrance end of an elongated housing 105 whose exit end is connected to an exemplary processing machine 110. Substrate S is guided along housing 105 by a series of guide rollers 115 to an exit slit 105B that connects housing 105 to the interior of machine 110. Thereafter, the guidance of the substrate is taken over by a guide roller 110A in that machine. Substrate S is illustratively comprised of plastic film. It should be noted that in alternative embodiments, differing substrates may be utilized. As such, the description of substrate S being comprised of plastic film should be taken as exemplary only.

The illustrated machine 110 is illustratively a forming and filling machine which may be of any known type. Machine 110 accepts the substrate S and illustratively forms it into a tube-shaped receptacle which is filled with a product after which the filled tube shaped receptacle is sealed transversely at spaced-apart locations therealong and cut at the seals to form a succession of individual product packages P which are dispensed from machine 110 as shown. As a result of the processing steps carried out by machine 110, the machine illustratively has a substrate demand that is non-continuous so that web is drawn along housing 105 in a non-continuous manner. The description of tube-shaped receptacles being formed, filled, and sealed transversely should be take as exemplary. Equivalently, substrate S could be formed into a range of open receptacles including packs, cups, stickpacks, and bags and sealed in any range of ways including transverse sealing, folding, and adhering another material to the open edge of the receptacle.

Mounted at an opening in the top wall of housing 105 directly above substrate S is an electron beam emitter 120. Emitter 120 may be of a known type such as those described in U.S. Pat. No. 5,962,995, entitled ELECTRON BEAM ACCELERATOR, U.S. Pat. No. 6,674,229, entitled ELECTRON BEAM EMITTER and U.S. Pat. No. 7,329,885, entitled ELECTRON BEAM EMITTER. The contents of these three patents are hereby incorporated by reference. Illustratively, the emitter comprises a housing 125 defining a vacuum chamber 130. A window shown generally at 135 at the lower end of housing 125 forms the lower wall of chamber 130 and opens into housing 110. The window includes a thin foil 140A, e.g. of titanium or aluminum, supported by a perforated support plate 140B, e.g. of copper. When activated, emitter 120 produces electrons e in chamber 130 which are accelerated toward window 135. The electrons pass through the window and are directed as a beam to the segment of substrate S lying in an ebeam irradiation zone 145 directly opposite the window. Thus, as the substrate travels through zone 145, the upper surface thereof receives a sufficient ebeam dose to sterilize that surface of the substrate.

It is well known that electron beams penetrate through materials in relation to accelerating voltage of electron beam and the density of the material being penetrated. For many packaging materials, electron beams with voltages on order of 150 kV will completely penetrate the material so as to sterilize the undersurface as well. If it is desired to sterilize the undersurface of substrate S and substrate S is of a thickness or density such that the electron beam does not sufficiently penetrate substrate S, a similar emitter may be mounted to housing 105 below the web as shown in phantom at 120', in which case both emitters may be operated in unison.

The emitter 120 (and 120') is powered by a power supply 150 and 150' under the control of a controller 155 which may be the same controller controlling machine 110.

As discussed previously, process machines such as machine 110 consume a web such as substrate S in a non-continuous fashion. That is, web is drawn into the machine at a given rate and the web advance stopped and/or slowed at certain intervals while the machine processes the web already in the machine. This non-continuous advance of the web into the machine affects the time spent by successive segments of the substrate S in the irradiation zone 145 and thus the ebeam dose received by those segments. If the dosage received by the substrate is too low, it may not be sterilized adequately. On the other hand, if the dose is too high, the excessive radiation may cause an adverse reaction in the substrate.

Therefore, in accordance with an illustrative embodiment of the present invention, in order to maintain the ebeam dose intensity received by the substrate in the irradiation zone 145 within an acceptable range, the current density or intensity of the ebeam at the is substrate is controlled as a function of the speed of the substrate through that zone. In exemplary environment 100, such control is accomplished in either one or both of two illustrative embodiments.

In a first illustrative embodiment, a power supply 150 is controlled to vary the voltage and current of the electron beam produced by emitter 120 as a function of the advance of the substrate S into machine 110. For this, the roller 110A in machine 110 drives a tachometer 160 whose output reflects the substrate demands of machine 110. The output of the tachometer 160 is applied to controller 155 which responds by controlling power supply 150 to reduce the voltage and/or the current of the electron beam from emitter 120 when the substrate advance slows and to increase that voltage and/or the current when such advance speeds up so that the current density of the ebeam at the substrate passing through the irradiation zone 145 is relatively uniform or remains within a desired range. In this embodiment, the controller may be programmed to simultaneously reduce the current and voltage in such a way as to keep constant thermal load on the emitter window foil 140A.

The controller 155 may also be programmed to control the emitter and/or modulator as a function of the predicted substrate demands of the machine 110. In order to monitor the intensity of the electron beam in zone 145, one or more sensors 165 may be provided at the perimeter of zone 145 in accordance with an illustrative embodiment of the present invention. A suitable such sensor is described in U.S. Pat. No. 6,919,570, entitled ELECTRON BEAM SENSOR, the contents of which are hereby incorporated by reference. The output of the sensor(s) 165 may be applied to controller 155 to help set the ebeam dosage limits for the particular substrate S.

A second illustrative embodiment for exemplary environment 100 to control the ebeam dosage applied by emitter 135 to substrate S in zone 145 is to position a beam modulator 170 between the emitter window 135 and the substrate S as shown. Modulator 170 illustratively may constitute a grid to which a variable voltage is applied by a power supply 175 under the control of controller 155. Thus, the modulator 170 may vary the current density or energy intensity of the ebeam to which the substrate is exposed by partially or completely blocking or scattering the electrons e in the ebeam so that fewer or none reach the substrate, depending on the speed S of the substrate as measured by tachometer 160.

Whichever of the illustrative techniques is used to control the ebeam dose applied to the substrate, care is taken to regulate the ebeam voltage so as not to thermally overstress the emitter exit window 135.

Thus, when the variations in the substrate advance are relatively small, controller 155, in response to the output of tachometer 160, may control power supply 150 so that the ebeam operates at a substantially constant voltage and current that does not apply excessive thermal stress to the emitter window 135. At the same time, the controller may control the power supply 175 to adjust the modulator 165 so as to keep the ebeam dosage applied to the substrate within a desired range.

When the speed of substrate S varies more dramatically, the dosage control may be achieved solely by controlling the power supply 150 to keep the current density of the ebeam at the substrate within an acceptable range that sterilizes that substrate without is causing any adverse effect.

In other situations, proper control of the ebeam intensity or current density at the substrate may require adjustment by the controller 155 of both the emitter and modulator power supplies. In all cases, however, the ebeam intensity at the window 135 should be kept with a range that does not thermally overstress the window.

In the event that the machine 110 includes an accumulator (not shown) at its input, the substrate S may be advanced at a constant speed into the accumulator in which case, the intensity of the ebeam from emitter 120 may be set at a constant value which sterilizes the substrate and does not thermally overstress the window 135.

Figure 2:
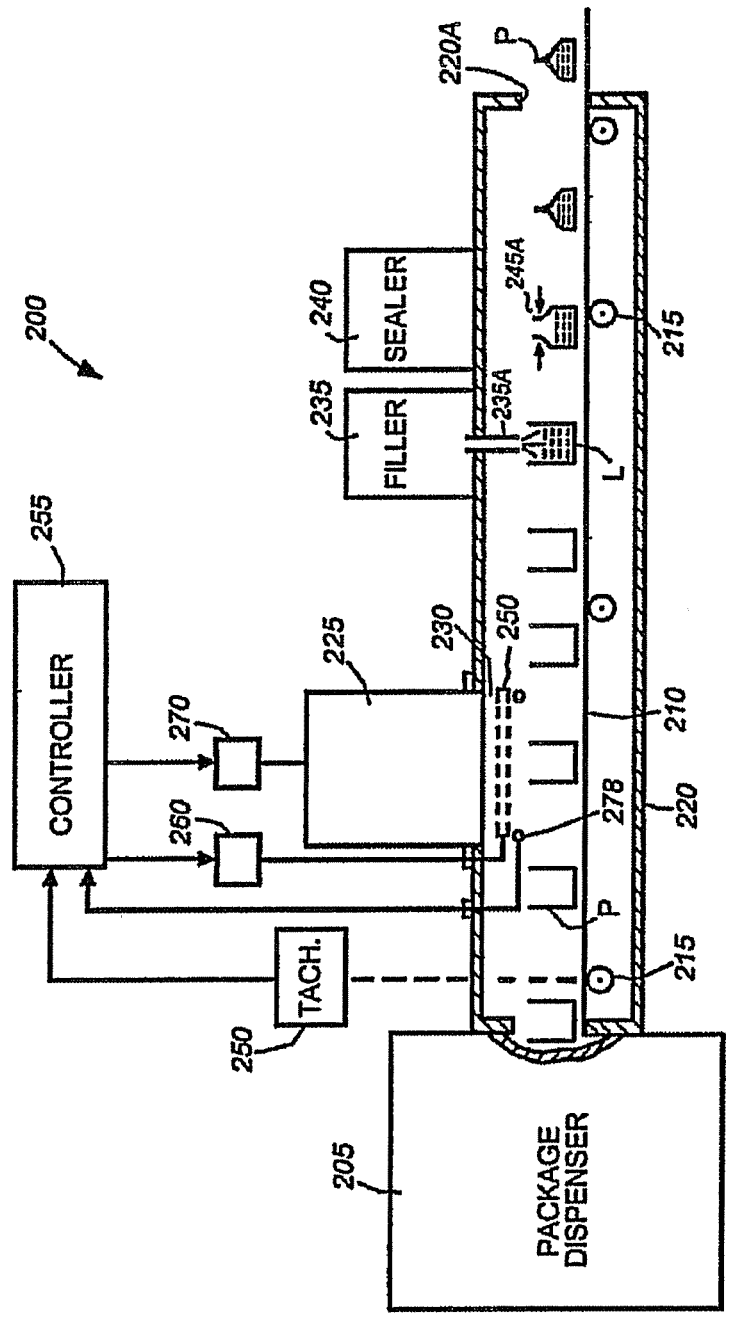
FIG. 2 is a schematic diagram of an exemplary electron beam sterilization apparatus environment in accordance with an illustrative embodiment of the present invention.

FIG. 2 is of an exemplary ebeam sterilization apparatus environment 200 which sterilizes product packaging in the form of a succession of open-top packages P being dispensed from a dispenser 205 onto a conveyor 210 which advances in a non-continuous manner. The conveyor is guided by guide rollers 215 along an aseptic housing 220 past an ebeam emitter 225 similar to emitter 120 which can direct an ebeam to packages P moving through an irradiation zone 230 in housing 220 opposite the emitter. The ebeam sterilizes the packages just before they are filled with a liquid L dispensed through fill-tube 235A of a filler mounted to housing 220. After being filled, the tops of the packages are then closed and sealed by the heated jaws 245A of a sealer 240 mounted to housing 220, after which the sealed packages exit the housing through an exit slit 220A. The drawing depicting the open top packages P as a cup shaped package is exemplary. Open-top packages may also include preformed pouches or bags that are filled through open tops or through spouts. Likewise process of sealing with heated jaws is exemplary. Equivalently, packages could be sealed in another manner such as by having another material adhered to the open edge of the receptacle or by having a preformed closure attached to the open end of the receptacle.

A tachometer 250 driven by one of the guide rollers 215 applies a conveyor speed-indicating signal to a controller 255 which may also receive a signal from an ebeam intensity sensor(s) 278 similar to sensor 165 in FIG. 1. Controller 255 may control dispenser 205, filler 235 and sealer 240 as well as a power supply 270 driving emitter 225 and a power supply 260 that may apply a blocking voltage to a beam modulator 250 in the irradiation zone 230.

The apparatus shown in environment 200 can apply a substantially uniform ebeam dose, or a dose within a selected range, to successive packages P passing through the irradiation zone 230 despite the non-continuous advance of conveyor 210. At the same time, it prevents the ebeam window of emitter 225 from being thermally overstressed.

B. Venting Irradiation Chamber

Figure 3:
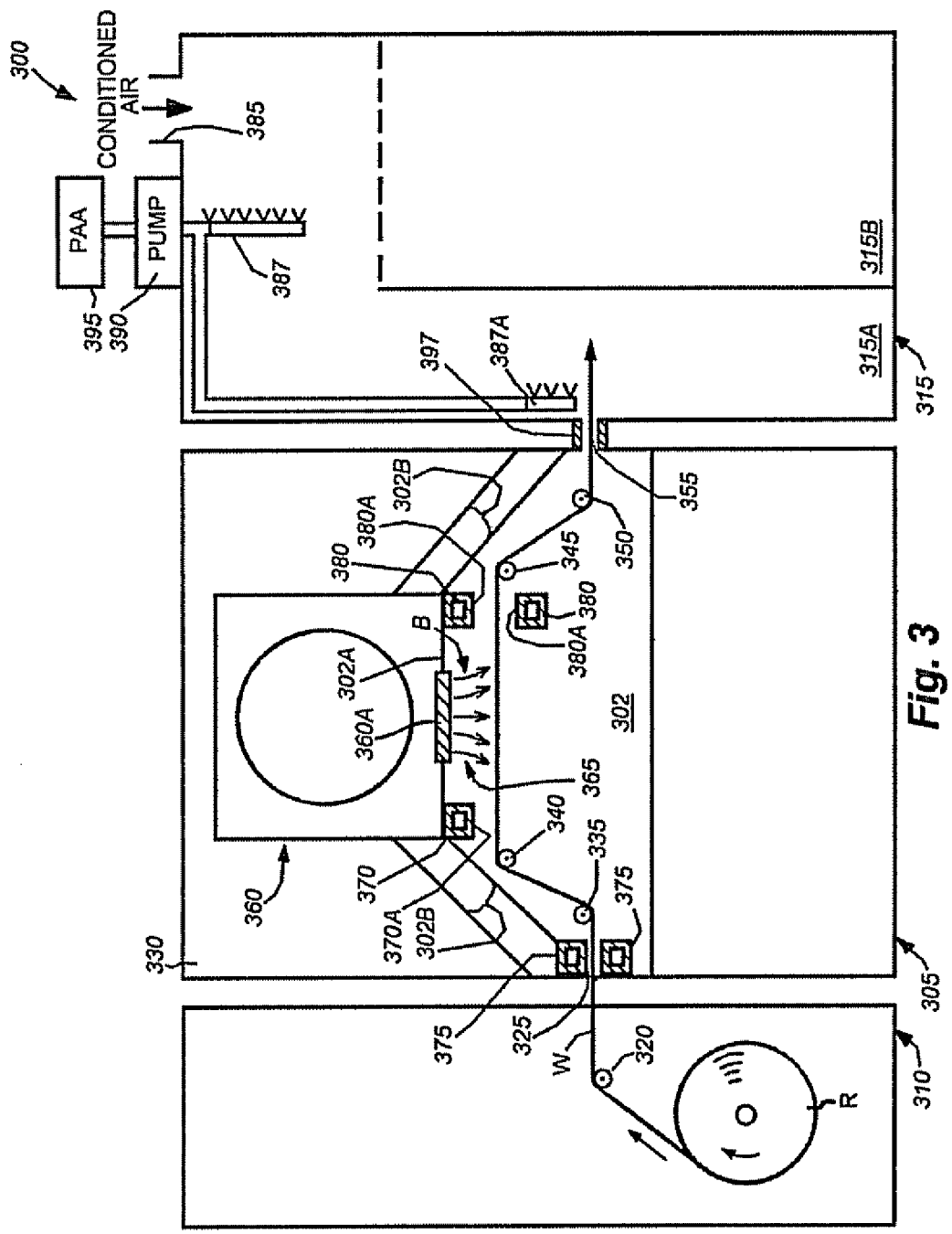
FIG. 3 is a schematic diagram of an exemplary vented web sterilization apparatus environment in accordance with an illustrative embodiment of the present invention.

Referring to FIG. 3 of the drawings, an illustrative subject vented web sterilization apparatus environment 300 is shown generally at 305 situated between a roll stand 310 and a packaging machine 315. A web W of any known type used for packaging is drawn from a roll R rotatably mounted to the roll stand 310. The web W from roll R is trained about a guide roller 320 on stand 310 and guided in a more or less horizontal direction to an entry slot 325 at one end of a housing 330 comprising apparatus 305. Slot 325 opens into one end of a shielded radiation tunnel 302 within the housing. After entering that tunnel, web W passes around a pair of angularly offset guide rollers 335 and 340 and travels horizontally to a pair of minor-image, angularly offset guide rollers 345 and 350 located at the opposite end of tunnel 302 where the web leaves the tunnel via an exit slot 355 in housing 330. After leaving apparatus 305, the web enters the packaging machine 315 via exit slot 355.

As shown in FIG. 3, web W is guided through tunnel 302 so that the stretch of web between rollers 340 and 345 lies in a horizontal plane spaced above the plane defined by the entrance and exit slots 325 and 355 respectively. Supported directly above tunnel 302 within housing 330 is an electron beam emitter 360 having a window 360A that constitutes part of the upper wall 302A of tunnel 302. Emitter 120 may be of a known type such as those described in U.S. Pat. No. 5,962,995, entitled ELECTRON BEAM ACCELERATOR, U.S. Pat. No. 6,674,229, entitled ELECTRON BEAM EMITTER and U.S. Pat. No. 7,329,885, entitled ELECTRON BEAM EMITTER, the contents of which is hereby incorporated by reference herein.

As is well known in the art, emitter 360 directs a beam B of electrons to the upper surface of web W while the web travels through an irradiation zone shown generally at 365 in tunnel 302. As web passes through that zone, its upper surface is exposed for a long enough time to electrons of sufficiently high energy to disinfect the web surface. As noted above, if it is desired to sterilize the undersurface of web W and web W is of a is thickness or density such that the electron beam does not sufficiently penetrate web W, a similar emitter may be mounted opposite the underside of web W.

During the operation of apparatus 305, the electrons in beam B may interact with air molecules and the web material to produce potentially dangerous secondary electrons, x-rays and other high energy particles. To prevent such unwanted radiation from leaving tunnel 302, the tunnel has walls 302B incorporating a radiation shielding material such as lead. Also, to prevent such radiation from escaping from the tunnel via slots 325 and 355, those slots may be formed as collimating slots. In addition, the relative angular positions of the guide rollers 335, 340, 345 and 350 adjacent to those slots are set so that high energy particles scattered from the web during the irradiation process are constrained to experience multiple reflections off the inner walls of tunnel 302 to dissipate the energy of those particles to safe levels before exiting tunnel 302.

Still referring to FIG. 3, an exhaust manifold 370 serving a multiplicity of web-facing exhaust ports 370A extends the full width of web W upstream webwise from the irradiation zone 365. Similar ported exhaust manifolds 375 may be present above and below entry slot 325 where the web enters tunnel 302. The manifolds 370 and 375 are connected by shielded ducting (not shown) to an exhaust fan so that the air from tunnel 302 may optionally be drawn through a suitable filter (and perhaps a catalytic converter) to capture pollutants such as bacteria, particulate matter and ozone gas.

It is a feature of the invention that one or more dual-purpose transverse manifolds 380 with web-facing ports 380A are supported within housing 302 just downstream from irradiation zone 365 in the direction of web travel. As will be described shortly, each manifold 380 functions as both an inlet manifold and an outlet manifold at different times during the operation of apparatus 305.

The packaging machine 315 may be of any conventional construction. Suffice it to say here that machine 315 includes a tower section 315A and a slitter/filler section 315B. Section 315A may include driven rollers which draw web W from roll R at a uniform rate through tunnel 302 and a web accumulator (not shown) which maintains a substantially constant web tension and satisfies the varying web requirements of the slitter/filler section 315B. Typically, filtered air at a desired temperature is introduced into machine 315 via an inlet opening 385. Preferably, also, before each web run, an SIP cycle is carried out whereby a sterilant is introduced into the incoming air stream by means of a nozzle 387 connected by way of a pump 390 to a sterilant source 395. A second such nozzle 387A may be present in section 315A at the exit and of conduit 397. When pump 390 is in operation, the sterilant is ejected from nozzles 387 and 387A into the air stream and distributed on the interior surfaces of the machine 305.

Usually, in prior apparatus of this type, some of that sterilant is drawn through conduit 397 into tunnel 302 of apparatus 305 where it covers surfaces in the irradiation zone 365 of that apparatus thereby producing the adverse consequences described above.

To avoid this eventuality, it is a feature of this invention that during the aforesaid SIP cycle, the manifold(s) 380 is/are connected to a vacuum source so that any sterilant entering tunnel 302 via exit slot 355 is swept away before it can reach the irradiation zone 365.

Preferably, each manifold 380 should be as close as possible to zone 365 so that the SIP sterilant can reach all surfaces downstream from zone 365 but cannot enter that zone. Thus, the tunnel 302 surfaces within zone 365 remain devoid of sterilant and are sterilized only by the electrons in beam B when emitter 360 is operative. In other words, the zone 365 portion of tunnel 302 only undergoes electron beam sterilization and thus minimizes sterilant residue accumulating on surfaces therein.

Then, during normal operation of the apparatus when the moving web (and all surfaces in zone 365) are being irradiated by beam B, cool air under pressure is supplied to the manifold(s) 380 so that the air issuing from the ports 380A thereof can sweep any ozone gas present in zone 365 or in the tunnel 302 generally toward the exhaust manifolds 370 and 375 at the entrance end of the apparatus. Thus, the manifolds 380 above and below the web both remove air from and deliver air to the tunnel 302 at different times during the operation of the overall apparatus.

Figure 4:
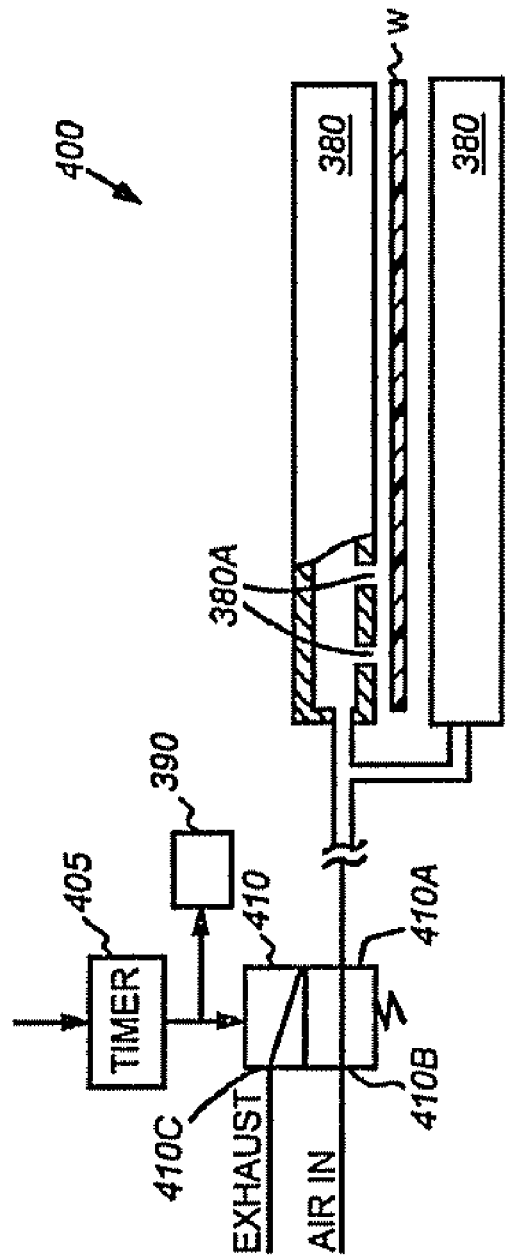
FIG. 4 is a schematic diagram of an exemplary manifold environment in accordance with an illustrative embodiment of the present invention.

Referring now to FIG. 4, to accomplish the two functions described above, the manifolds 380 are connected to the outlet port 410A of a two-position solenoid valve 410 having two inlet ports 410B and 410C. Inlet port 410B is connected to a supply of cool air under pressure, the other inlet port 410C is connected to an exhaust fan which may be the same one that serves exhaust manifolds 370 and 375 described above. As shown in FIG. 4, the internal valve member of valve 410 is biased so that the valve outlet port 410A is normally coupled via inlet port 410B to an air source as shown so that the manifolds 380 function air inlet manifolds during the normal operation of the apparatus 305.

However, during the pre-sterilization (SIP) process, the valve 410 solenoid may be energized for a selected period, e.g., 15-25 min., most preferably 20 min., by a signal from an adjustable timer 405 which is activated at the beginning of the SIP cycle. That same signal from timer 405 or controller 255 may activate the pump 390 in FIG. 3, which delivers sterilant into the machine 315 and apparatus 305. Thus, throughout the SIP cycle when sterilant is free to enter apparatus 305 through its web exit slot 355, the vacuum drawn at manifold(s) 380a reduces the amount of the sterilant from entering the radiation zone 365 of tunnel 302. Thus, all of the surfaces in that zone remain essentially free of sterilant. Later, when the emitter 360 is activated, the surfaces within that zone are dry-sterilized by the electrons in beam B. Of course, sterilization is not necessary for the portion of tunnel 302 upstream from zone 365 because the web W that enters the apparatus is unsterilized.

At the end of the SIP cycle, the timer 405 times out thereby shutting off the flow of sterilant from pump 390 and causing the valve 410 to assume its normal condition which reverses the air flow at manifold(s) 380. Resultantly, cool air issues from the manifold ports 380A which assists in removing ozone gas from tunnel 302 when the web is being sterilized by ebeam B.

It will thus be seen from the foregoing that even though apparatus 305 is being used with a packaging machine 315 which is sterilized using wet sterilization, that sterilant is reduced from entering the apparatus' irradiation zone 365 where it could leave a residue that may damage the electron beam equipment. Then, during normal operation of apparatus 305, the same manifolds 380 that prevent sterilant from entering zone 365 function to help sweep ozone from that zone during normal operation of the apparatus.

The foregoing description has been directed to particular embodiments of this invention. It will be apparent, however, that other variations and modifications may be made to the described embodiments, with the attainment of some or all of their advantages. Additionally, the procedures, processes and/or modules described herein may be implemented in hardware, software, embodied as a computer-readable medium having program instructions, firmware, or a combination thereof. It should be noted that the various web movement mechanisms, e.g., rollers, etc., may be varied and/or modified in alternative embodiments. Therefore, it is the object of the appended claims to cover all such variations and modifications as come within the true spirit and scope of the invention.

What is claimed is:

1. An apparatus for sterilizing a web material, the apparatus comprising:
   a housing into which the web material is drawn into a machine in a non-continuous manner;
   a first electron beam emitter oriented to generate a first electron beam to sterilize a first surface of the web material as it traverses the housing;
   a tachometer operatively interconnected with a roller in the machine, the tachometer configured to identify a speed at which the web material is being drawn by the machine;
   a first beam modulator for modulating a density of the first electron beam applied from a window of the first electron beam emitter to the first surface of the web material, the first beam modulator provided between the window of the first electron beam emitter and the web material;

a first power supply for powering the first beam modulator; and a controller operatively interconnected with the tachometer and the first power supply and configured to control a beam energy output from a transmission factor of the first beam modulator so as to keep the density of the first electron beam on the web material within a desired range while the web material is in an irradiation zone, the controller further configured to control a current and voltage of the first electron beam so as to keep a constant thermal load on a thin foil of the first electron beam emitter while the web material is in the irradiation zone.

2. The apparatus of claim 1 wherein the web material comprises a substrate.

3. The apparatus of claim 2 wherein the substrate comprises plastic film.

4. The apparatus of claim 1 further comprising:

a second electron beam emitter oriented to generate a second electron beam to sterilize a second surface of the web material as it traverses the housing;

a second beam modulator for modulating a density of the second electron beam applied from a window of the second electron beam emitter to the second surface of the web material, the second beam modulator provided between the window of the second electron beam emitter and the web material; and a second power supply for powering the second beam modulator.

5. The apparatus of claim 4 wherein the controller is further configured to control a beam energy output from a transmission factor of the second beam modulator so as to keep the density of the second electron beam on the web material within a desired range while the web material is in an irradiation zone.

6. The apparatus of claim 1 wherein the machine comprises a forming and filling machine.

7. The apparatus of claim 1 wherein the controller is configured to modify a voltage applied to the first beam modulator in response to changes of the speed of the web material measured by the tachometer.

* * * * *